(12) United States Patent
Wei

(10) Patent No.: US 12,122,817 B2
(45) Date of Patent: Oct. 22, 2024

(54) LONG-LASTING GLP1 ANALOGUE DRUG FOR TYPE-2 DIABETES

(71) Applicant: Serpentide Inc., Hangzhou (CN)

(72) Inventor: Yang Wei, Yorktown Heights, NY (US)

(73) Assignee: SERPENTIDE INC., Hangzhou (CN)

( * ) Notice: Subject to any disclaimer, the term of this patent is extended or adjusted under 35 U.S.C. 154(b) by 393 days.

(21) Appl. No.: 17/184,248

(22) Filed: Feb. 24, 2021

(65) Prior Publication Data

US 2022/0267402 A1 Aug. 25, 2022
US 2022/0389071 A9 Dec. 8, 2022

Related U.S. Application Data

(60) Provisional application No. 63/081,363, filed on Sep. 22, 2020.

(51) Int. Cl.
| | | |
|---|---|---|
| A61K 38/26 | (2006.01) | |
| A61K 39/395 | (2006.01) | |
| A61K 45/06 | (2006.01) | |
| A61P 3/10 | (2006.01) | |
| C07K 14/605 | (2006.01) | |
| C07K 16/28 | (2006.01) | |
| A61K 39/00 | (2006.01) | |

(52) U.S. Cl.
CPC ............ *C07K 14/605* (2013.01); *A61K 38/26* (2013.01); *A61K 39/3955* (2013.01); *A61K 45/06* (2013.01); *A61P 3/10* (2018.01); *C07K 16/28* (2013.01); *C07K 16/2869* (2013.01); *A61K 2039/505* (2013.01); *C07K 2317/31* (2013.01); *C07K 2317/55* (2013.01); *C07K 2319/30* (2013.01); *C07K 2319/35* (2013.01); *C07K 2319/50* (2013.01)

(58) Field of Classification Search
CPC ...... A61K 38/26; C07K 14/605; C07K 16/28; C07K 2319/30
See application file for complete search history.

(56) References Cited

U.S. PATENT DOCUMENTS

| | | | |
|---|---|---|---|
| 2010/0068289 A1 | 3/2010 | Geigle et al. | |
| 2015/0183847 A1 | 7/2015 | Qin | |
| 2019/0085082 A1 | 3/2019 | Bicknell et al. | |
| 2019/0309279 A1 | 10/2019 | Sinha et al. | |

FOREIGN PATENT DOCUMENTS

| | | | |
|---|---|---|---|
| CN | 1483041 A | * | 3/2004 |
| WO | 2020028806 A1 | | 2/2020 |
| WO | 2020063628 A1 | | 4/2020 |

OTHER PUBLICATIONS

Perfetti et al., Eur. J. Endocr. 143, 717-725, (2000).*
Gutniak et al., New England J. Med. 30 326:1316-1322, (1992).*
Padlan, et al., "Identification of specificity-determining residues in antibodies," FASEB Journal, Jan. 1995, vol. 9, pp. 133-139.
Gonnet, et al., "Exhaustive Matching of the Entire Protein Sequence Database," Science, Jun. 5, 1992, New Series, vol. 256, No. 5062, pp. 1443-1445.
Vajdos, et al., Comprehensive Functional Maps of the Antigen-binding Site of an Anti-ErbB2 Antibody Obtained with Shotgun Scanning Mutagenesis; J Mol Biol (2002) 320:415-428.
Al-Lazikani et al., "Standard Conformations for the Canonical Structures of Immunoglobulins," J. Mol. Biol. (1997) 273, pp. 927-948, Academic Press.
Martin, et al., "Modeling antibody hypervariable loops: A combined algorithm," Proc. Natl. Acad. Sci. USA (1989), vol. 86, pp. 9268-9272.
Altschul et al., "Basic local alignment search tool," J. Mol. Biol. (1990) 215, pp. 403-410.
Altschul et al., "Gapped BLAST and PSI-BLAST: a new generation of protein database search programs," Nucleic Acids Res. (1997), vol. 25, pp. 3389-3402, Oxford University Press.
Deacon et al., "Dipeptidyl peptidase IV resistant analogues of glucagon-like peptide-1 which have extended metabolic stability . . . ," Diabetologia (1998) vol. 14, pp. 271-278.
Wut et al., "Receptor-mediated in Vitro Gene Transformation by a Soluble DNA Carrier System," J. Biol. Chem. (1987), vol. 262, No. 10, pp. 4429-4432.
Langer, Robert, " New methods of drug delivery," Science, Sep. 28, 1990, New Series, vol. 249, No. 4976, pp. 1527-1533.
International Search Report mailed Feb. 25, 2019 for PCT/US2018/052110.
Written Opinion of the International Searching Authority mailed Feb. 25, 2019 for PCT/US2018/052110.
Chung et al., "The N-terminal alanine-extended GLP-1/IgG-Fc fusion protein confers resistance . . . ," Regulatory Peptides, Oct. 1, 2011, vol. 170, pp. 1-3.
Kim et al., "Novel AGLP-1 albumin fusion protein as a long-lasting agent for type 2 diabetes," BMB Reports, Dec. 31, 2013, vol. 46, No. 12, pp. 606-610, publ. in Korea.
Glaesner et al., "Engineering and characterization of the long-acting glucagon-like peptide-1 analogue . . . ," Diabetes Metab Res Rev, Apr. 30, 2010, vol. 26, No. 4, pp. 287-296.
Manandhar et al., "Glucagon-like Peptide-1 (GLP-1) Analogs: Recent Advances, New Possibilities and Therapeutic Implications," J. Med. Chem. (2015) vol. 58, No. 3, pp. 1020-1037.

* cited by examiner

*Primary Examiner* — Gyan Chandra
(74) *Attorney, Agent, or Firm* — Panitch Schwarze Belisario & Nadel LLP; Stephany G. Small; Ava E. Lutz

(57) ABSTRACT

Modified glucagon-like peptide (GLP1) fusion proteins with modified GLP1 polypeptides and related methods of use are described. Aspects of the disclosure further relate to fusion proteins that are GLP1 receptor agonists with a modified GLP1 fused to a stabilizing domain such as an extra cellular domain or antibody. Fusion proteins with modified GLP1 that are useful for treating or ameliorating a symptom or indication of a blood sugar disorder such as obesity and diabetes are also provided.

12 Claims, 11 Drawing Sheets

Specification includes a Sequence Listing.

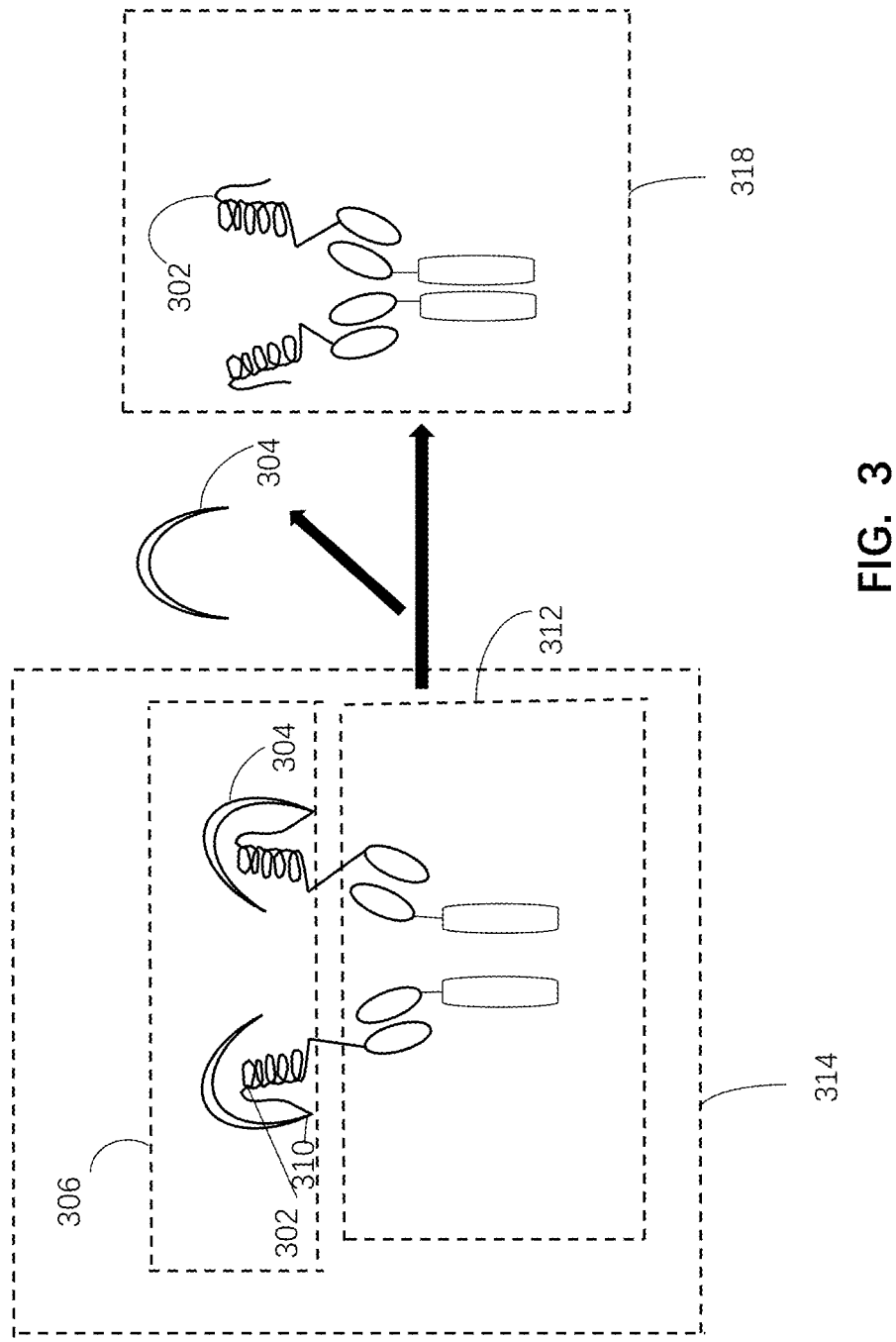

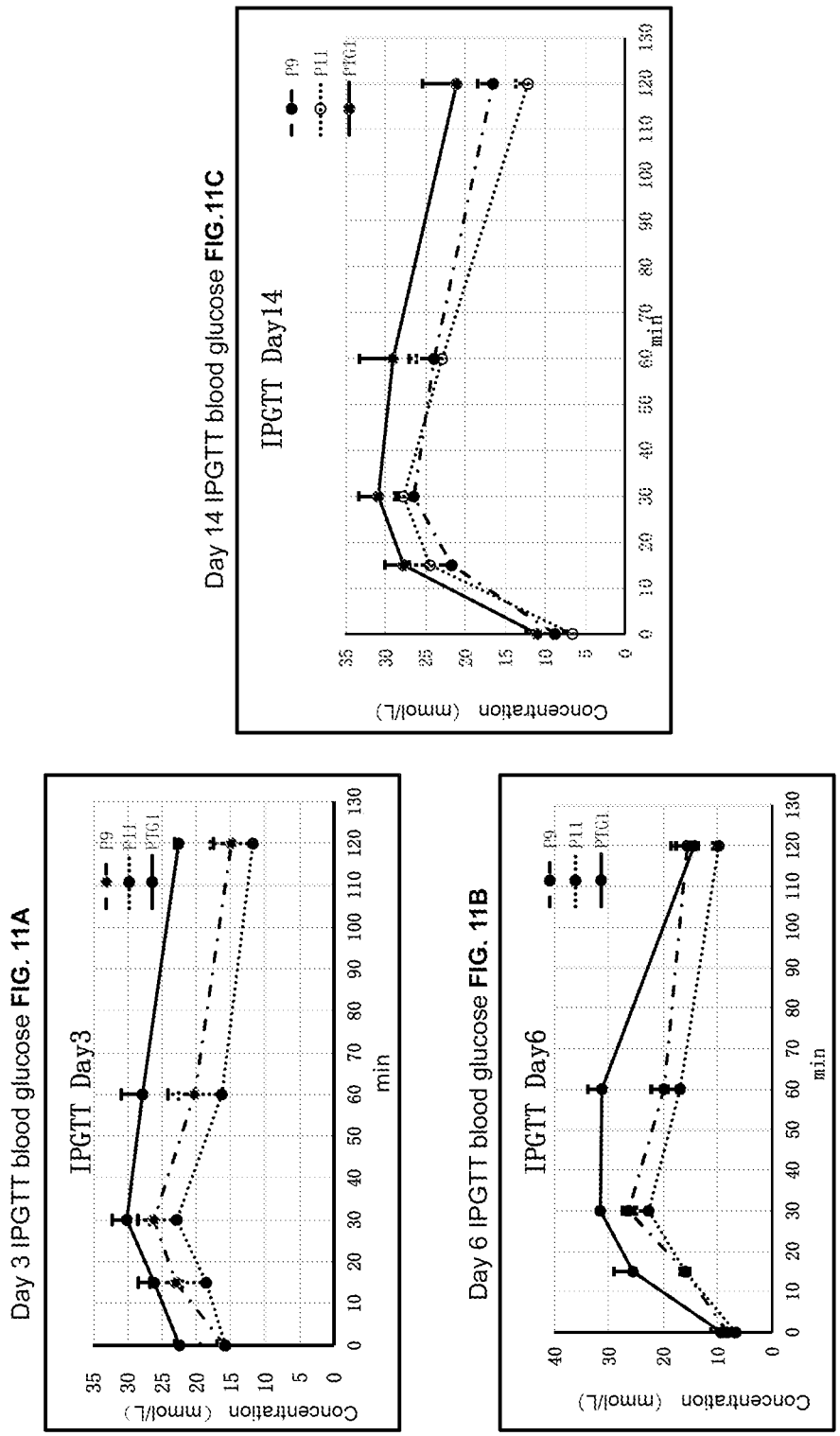

SEQUENCE LISTING

<160> NUMBER OF SEQ ID NOS: 16

<210> SEQ ID NO 1
<211> LENGTH: 229
<212> TYPE: PRT
<213> ORGANISM: Artificial Sequence
<220> FEATURE:
<223> OTHER INFORMATION: pTG1(hFc)

<400> SEQUENCE: 1

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly
```

<210> SEQ ID NO 2
<211> LENGTH: 275
<212> TYPE: PRT
<213> ORGANISM: Artificial Sequence
<220> FEATURE:
<223> OTHER INFORMATION: Trulicity

<400> SEQUENCE: 2

```
His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser Ala Glu
        35                  40                  45

Ser Lys Tyr Gly Pro Pro Cys Pro Pro Cys Pro Ala Pro Glu Ala Ala
        50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275
```

<210> SEQ ID NO 3
<211> LENGTH: 116
<212> TYPE: PRT
<213> ORGANISM: Artificial Sequence
<220> FEATURE:
<223> OTHER INFORMATION: hGLP1R ECD

<400> SEQUENCE: 3

```
Arg Pro Gln Gly Ala Thr Val Ser Leu Trp Glu Thr Val Gln Lys Trp
 1               5                  10                  15
```

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys Arg Gly Glu Arg Ser
            100                 105                 110

Ser Pro Glu Glu
        115

<210> SEQ ID NO 4
<211> LENGTH: 116
<212> TYPE: PRT
<213> ORGANISM: Artificial Sequence
<220> FEATURE:
<223> OTHER INFORMATION: hGLP1R ECD(R108G)

<400> SEQUENCE: 4

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys Gly Gly Glu Arg Ser
            100                 105                 110

Ser Pro Glu Glu
        115

<210> SEQ ID NO 5
<211> LENGTH: 107
<212> TYPE: PRT
<213> ORGANISM: Artificial Sequence
<220> FEATURE:
<223> OTHER INFORMATION: hGLP1R ECD(1-107)

<400> SEQUENCE: 5

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys
            100                 105

<210> SEQ ID NO 6
<211> LENGTH: 410
<212> TYPE: PRT
<213> ORGANISM: Artificial Sequence
<220> FEATURE:
<223> OTHER INFORMATION: pTG3 hGLP1R ECD-3xG4S-RKRR-Trulicity

<400> SEQUENCE: 6

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys Arg Gly Glu Arg Ser
            100                 105                 110

Ser Pro Glu Glu Gly Gly Gly Ser Gly Gly Gly Ser Gly Gly
        115                 120                 125

Gly Gly Ser Arg Lys Arg Arg His Gly Glu Gly Thr Phe Thr Ser Asp
    130                 135                 140

Val Ser Ser Tyr Leu Glu Glu Gln Ala Ala Lys Glu Phe Ile Ala Trp
145                 150                 155                 160

Leu Val Lys Gly Gly Gly Gly Gly Gly Ser Gly Gly Gly Gly Ser
                165                 170                 175

Gly Gly Gly Gly Ser Ala Glu Ser Lys Tyr Gly Pro Pro Cys Pro Pro
            180                 185                 190

Cys Pro Ala Pro Glu Ala Ala Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser Gln Glu Asp Pro Glu Val Gln Phe Asn
225                 230                 235                 240

Trp Tyr Val Asp Gly Val Glu Val His Asn Ala Lys Thr Lys Pro Arg
                245                 250                 255

Glu Glu Gln Phe Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Gly Leu Pro Ser Ser Ile Glu Lys Thr Ile Ser Lys Ala Lys
    290                 295                 300

Gly Gln Pro Arg Glu Pro Gln Val Tyr Thr Leu Pro Pro Ser Gln Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
355                 360                 365

Phe Leu Tyr Ser Arg Leu Thr Val Asp Lys Ser Arg Trp Gln Glu Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Leu Gly
            405                 410

<210> SEQ ID NO 7
<211> LENGTH: 410
<212> TYPE: PRT
<213> ORGANISM: Artificial Sequence
<220> FEATURE:
<223> OTHER INFORMATION: p7 hGLP1R ECD(R108G)-3xG4S-RGERTrulicity

<400> SEQUENCE: 7

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Gly Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
            85                  90                  95

Trp Arg Asp Leu Ser Glu Cys Glu Glu Ser Lys Gly Gly Glu Arg Ser
            100                 105                 110

Ser Pro Glu Glu Gly Gly Gly Ser Gly Gly Gly Ser Gly Gly
        115                 120                 125

Gly Gly Ser Arg Gly Glu Arg His Gly Glu Gly Thr Phe Thr Ser Asp
    130                 135                 140

Val Ser Tyr Leu Glu Glu Gln Ala Ala Lys Glu Phe Ile Ala Trp
145                 150                 155                 160

Leu Val Lys Gly Gly Gly Gly Gly Ser Gly Gly Gly Gly Ser
            165                 170                 175

Gly Gly Gly Gly Ser Ala Glu Ser Lys Tyr Gly Pro Pro Cys Pro Pro
        180                 185                 190

Cys Pro Ala Pro Glu Ala Ala Gly Gly Pro Ser Val Phe Leu Phe Pro
        195                 200                 205

Pro Lys Pro Lys Asp Thr Leu Met Ile Ser Arg Thr Pro Glu Val Thr
        210                 215                 220

Cys Val Val Val Asp Val Ser Gln Glu Asp Pro Glu Val Gln Phe Asn
225                 230                 235                 240

Trp Tyr Val Asp Gly Val Glu Val His Asn Ala Lys Thr Lys Pro Arg
                245                 250                 255

Glu Glu Gln Phe Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

```
Asn Lys Gly Leu Pro Ser Ser Ile Glu Lys Thr Ile Ser Lys Ala Lys
            290                 295                 300

Gly Gln Pro Arg Glu Pro Gln Val Tyr Thr Leu Pro Pro Ser Gln Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Arg Leu Thr Val Asp Lys Ser Arg Trp Gln Glu Gly
370                 375                 380

Asn Val Phe Ser Cys Ser Val Met His Glu Ala Leu His Asn His Tyr
385                 390                 395                 400

Thr Gln Lys Ser Leu Ser Leu Ser Leu Gly
                405                 410

<210> SEQ ID NO 8
<211> LENGTH: 406
<212> TYPE: PRT
<213> ORGANISM: Artificial Sequence
<220> FEATURE:
<223> OTHER INFORMATION: p8 hGLP1R ECD(R108G)-3xG4S-Trulicity

<400> SEQUENCE: 8

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
                20                  25                  30

Pro Ala Thr Asp Leu Phe Cys Asn Arg Thr Phe Asp Glu Tyr Ala Cys
            35                  40                  45

Trp Pro Asp Gly Glu Pro Gly Ser Phe Val Asn Val Ser Cys Pro Trp
        50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys Gly Gly Glu Arg Ser
            100                 105                 110

Ser Pro Glu Glu Gly Gly Gly Ser Gly Gly Gly Ser Gly Gly
        115                 120                 125

Gly Gly Ser His Gly Glu Gly Thr Phe Thr Ser Asp Val Ser Ser Tyr
    130                 135                 140

Leu Glu Glu Gln Ala Ala Lys Glu Phe Ile Ala Trp Leu Val Lys Gly
145                 150                 155                 160

Gly Gly Gly Gly Gly Ser Gly Gly Gly Gly Ser Gly Gly Gly Gly
                165                 170                 175

Ser Ala Glu Ser Lys Tyr Gly Pro Pro Cys Pro Pro Cys Pro Ala Pro
            180                 185                 190

Glu Ala Ala Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser Gln Glu Asp Pro Glu Val Gln Phe Asn Trp Tyr Val Asp
225                 230                 235                 240
```

```
Gly Val Glu Val His Asn Ala Lys Thr Lys Pro Arg Glu Glu Gln Phe
            245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Gly Leu
            275                 280                 285

Pro Ser Ser Ile Glu Lys Thr Ile Ser Lys Ala Lys Gly Gln Pro Arg
            290                 295                 300

Glu Pro Gln Val Tyr Thr Leu Pro Pro Ser Gln Glu Glu Met Thr Lys
305                 310                 315                 320

Asn Gln Val Ser Leu Thr Cys Leu Val Lys Gly Phe Tyr Pro Ser Asp
            325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
            355                 360                 365

Arg Leu Thr Val Asp Lys Ser Arg Trp Gln Glu Gly Asn Val Phe Ser
            370                 375                 380

Cys Ser Val Met His Glu Ala Leu His Asn His Tyr Thr Gln Lys Ser
385                 390                 395                 400

Leu Ser Leu Ser Leu Gly
            405

<210> SEQ ID NO 9
<211> LENGTH: 400
<212> TYPE: PRT
<213> ORGANISM: Artificial Sequence
<220> FEATURE:
<223> OTHER INFORMATION: p9 hGLP1R ECD(1-116)-3xG4S-RGERTrulicity

<400> SEQUENCE: 9

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
            35                  40                  45

Trp Pro Asp Gly Glu Pro Gly Ser Phe Val Asn Val Ser Cys Pro Trp
            50                  55                  60

Tyr Leu Pro Trp Ala Ser Ser Val Pro Gln Gly His Val Tyr Arg Phe
65              70                  75                  80

Cys Thr Ala Glu Gly Leu Trp Leu Gln Lys Asp Asn Ser Ser Leu Pro
            85                  90                  95

Trp Arg Asp Leu Ser Glu Cys Glu Glu Ser Lys Gly Gly Gly Gly Ser
            100                 105                 110

Gly Gly Gly Gly Ser Gly Gly Gly Ser Arg Gly Glu Arg His Gly
            115                 120                 125

Glu Gly Thr Phe Thr Ser Asp Val Ser Ser Tyr Leu Glu Glu Gln Ala
            130                 135                 140

Ala Lys Glu Phe Ile Ala Trp Leu Val Lys Gly Gly Gly Gly Gly
145                 150                 155                 160

Gly Ser Gly Gly Gly Gly Ser Gly Gly Gly Ser Ala Glu Ser Lys
            165                 170                 175

Tyr Gly Pro Pro Cys Pro Pro Cys Pro Ala Pro Glu Ala Ala Gly Gly
            180                 185                 190
```

```
Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser Gln Glu
    210                 215                 220

Asp Pro Glu Val Gln Phe Asn Trp Tyr Val Asp Gly Val Glu Val His
225                 230                 235                 240

Asn Ala Lys Thr Lys Pro Arg Glu Glu Gln Phe Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Lys Val Ser Asn Lys Gly Leu Pro Ser Ser Ile Glu
        275                 280                 285

Lys Thr Ile Ser Lys Ala Lys Gly Gln Pro Arg Glu Pro Gln Val Tyr
    290                 295                 300

Thr Leu Pro Pro Ser Gln Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Arg Leu Thr Val Asp Lys
        355                 360                 365

Ser Arg Trp Gln Glu Gly Asn Val Phe Ser Cys Ser Val Met His Glu
    370                 375                 380

Ala Leu His Asn His Tyr Thr Gln Lys Ser Leu Ser Leu Ser Leu Gly
385                 390                 395                 400

<210> SEQ ID NO 10
<211> LENGTH: 408
<212> TYPE: PRT
<213> ORGANISM: Artificial Sequence
<220> FEATURE:
<223> OTHER INFORMATION: p10 hGLP1R ECD(R108G)-3xG4S-RR-Trulicity

<400> SEQUENCE: 10

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
            20                  25                  30

Pro Ala Thr Asp Leu Phe Cys Asn Arg Thr Phe Asp Glu Tyr Ala Cys
        35                  40                  45

Trp Pro Asp Gly Glu Pro Gly Ser Phe Val Asn Val Ser Cys Pro Trp
    50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
                85                  90                  95

Trp Arg Asp Leu Ser Glu Cys Glu Glu Ser Lys Gly Gly Glu Arg Ser
            100                 105                 110

Ser Pro Glu Glu Gly Gly Gly Ser Gly Gly Gly Ser Gly Gly
        115                 120                 125

Gly Gly Ser Arg Arg His Gly Glu Gly Thr Phe Thr Ser Asp Val Ser
    130                 135                 140

Ser Tyr Leu Glu Glu Gln Ala Ala Lys Glu Phe Ile Ala Trp Leu Val
145                 150                 155                 160
```

Lys Gly Gly Gly Gly Gly Gly Ser Gly Gly Gly Ser Gly Gly
              165                 170                 175

Gly Gly Ser Ala Glu Ser Lys Tyr Gly Pro Pro Cys Pro Cys Pro
          180                 185                 190

Ala Pro Glu Ala Ala Gly Gly Pro Ser Val Phe Leu Phe Pro Pro Lys
          195                 200                 205

Pro Lys Asp Thr Leu Met Ile Ser Arg Thr Pro Glu Val Thr Cys Val
      210                 215                 220

Val Val Asp Val Ser Gln Glu Asp Pro Glu Val Gln Phe Asn Trp Tyr
225                 230                 235                 240

Val Asp Gly Val Glu Val His Asn Ala Lys Thr Lys Pro Arg Glu Glu
              245                 250                 255

Gln Phe Asn Ser Thr Tyr Arg Val Val Ser Val Leu Thr Val Leu His
          260                 265                 270

Gln Asp Trp Leu Asn Gly Lys Glu Tyr Lys Cys Lys Val Ser Asn Lys
      275                 280                 285

Gly Leu Pro Ser Ser Ile Glu Lys Thr Ile Ser Lys Ala Lys Gly Gln
              290                 295                 300

Pro Arg Glu Pro Gln Val Tyr Thr Leu Pro Pro Ser Gln Glu Glu Met
305                 310                 315                 320

Thr Lys Asn Gln Val Ser Leu Thr Cys Leu Val Lys Gly Phe Tyr Pro
              325                 330                 335

Ser Asp Ile Ala Val Glu Trp Glu Ser Asn Gly Gln Pro Glu Asn Asn
          340                 345                 350

Tyr Lys Thr Thr Pro Pro Val Leu Asp Ser Asp Gly Ser Phe Phe Leu
      355                 360                 365

Tyr Ser Arg Leu Thr Val Asp Lys Ser Arg Trp Gln Glu Gly Asn Val
370                 375                 380

Phe Ser Cys Ser Val Met His Glu Ala Leu His Asn His Tyr Thr Gln
385                 390                 395                 400

Lys Ser Leu Ser Leu Ser Leu Gly
              405

<210> SEQ ID NO 11
<211> LENGTH: 409
<212> TYPE: PRT
<213> ORGANISM: Artificial Sequence
<220> FEATURE:
<223> OTHER INFORMATION: p11 hGLP1R ECD(R108G)-3xG4S-RKRTrulicity

<400> SEQUENCE: 11

Arg Pro Gln Gly Ala Thr Val Ser Leu Trp Glu Thr Val Gln Lys Trp
1               5                   10                  15

Arg Glu Tyr Arg Arg Gln Cys Gln Arg Ser Leu Thr Glu Asp Pro Pro
              20                  25                  30

Pro Ala Thr Asp Leu Phe Cys Asn Arg Thr Phe Asp Glu Tyr Ala Cys
          35                  40                  45

Trp Pro Asp Gly Glu Pro Gly Ser Phe Val Asn Val Ser Cys Pro Trp
      50                  55                  60

Tyr Leu Pro Trp Ala Ser Ser Val Pro Gln Gly His Val Tyr Arg Phe
65                  70                  75                  80

Cys Thr Ala Glu Gly Leu Trp Leu Gln Lys Asp Asn Ser Ser Leu Pro
              85                  90                  95

Trp Arg Asp Leu Ser Glu Cys Glu Glu Ser Lys Gly Gly Glu Arg Ser
          100                 105                 110

```
Ser Pro Glu Gly Gly Gly Ser Gly Gly Gly Ser Gly
    115                 120                 125
Gly Gly Ser Arg Lys Arg His Gly Glu Gly Thr Phe Thr Ser Asp Val
    130                 135                 140
Ser Ser Tyr Leu Glu Glu Gln Ala Ala Lys Glu Phe Ile Ala Trp Leu
145                 150                 155                 160
Val Lys Gly Gly Gly Gly Gly Gly Ser Gly Gly Gly Gly Ser Gly
                    165                 170                 175
Gly Gly Gly Ser Ala Glu Ser Lys Tyr Gly Pro Pro Cys Pro Pro Cys
                180                 185                 190
Pro Ala Pro Glu Ala Ala Gly Gly Pro Ser Val Phe Leu Phe Pro Pro
            195                 200                 205
Lys Pro Lys Asp Thr Leu Met Ile Ser Arg Thr Pro Glu Val Thr Cys
    210                 215                 220
Val Val Val Asp Val Ser Gln Glu Asp Pro Glu Val Gln Phe Asn Trp
225                 230                 235                 240
Tyr Val Asp Gly Val Glu Val His Asn Ala Lys Thr Lys Pro Arg Glu
                    245                 250                 255
Glu Gln Phe Asn Ser Thr Tyr Arg Val Val Ser Val Leu Thr Val Leu
                260                 265                 270
His Gln Asp Trp Leu Asn Gly Lys Glu Tyr Lys Cys Lys Val Ser Asn
            275                 280                 285
Lys Gly Leu Pro Ser Ser Ile Glu Lys Thr Ile Ser Lys Ala Lys Gly
    290                 295                 300
Gln Pro Arg Glu Pro Gln Val Tyr Thr Leu Pro Pro Ser Gln Glu Glu
305                 310                 315                 320
Met Thr Lys Asn Gln Val Ser Leu Thr Cys Leu Val Lys Gly Phe Tyr
                    325                 330                 335
Pro Ser Asp Ile Ala Val Glu Trp Glu Ser Asn Gly Gln Pro Glu Asn
                340                 345                 350
Asn Tyr Lys Thr Thr Pro Pro Val Leu Asp Ser Asp Gly Ser Phe Phe
            355                 360                 365
Leu Tyr Ser Arg Leu Thr Val Asp Lys Ser Arg Trp Gln Glu Gly Asn
    370                 375                 380
Val Phe Ser Cys Ser Val Met His Glu Ala Leu His Asn His Tyr Thr
385                 390                 395                 400
Gln Lys Ser Leu Ser Leu Ser Leu Gly
                405

<210> SEQ ID NO 12
<211> LENGTH: 5
<212> TYPE: PRT
<213> ORGANISM: Artificial Sequence
<220> FEATURE:
<223> OTHER INFORMATION: linker

<400> SEQUENCE: 12

Gly Gly Gly Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: linker
```

```
<400> SEQUENCE: 13

Gly Gly Gly Gly Ser Gly Gly Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: linker

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 4
<212> TYPE: PRT
<213> ORGANISM: Artificial Sequence
<220> FEATURE:
<223> OTHER INFORMATION: variant of Factor Xa digestion site

<400> SEQUENCE: 15

Arg Lys Arg Arg
1

<210> SEQ ID NO 16
<211> LENGTH: 4
<212> TYPE: PRT
<213> ORGANISM: Artificial Sequence
<220> FEATURE:
<223> OTHER INFORMATION: variant of Factor Xa digestion site

<400> SEQUENCE: 16

Arg Gly Glu Arg
1
```

LONG-LASTING GLP1 ANALOGUE DRUG FOR TYPE-2 DIABETES

CROSS-REFERENCE TO RELATED APPLICATION

This application claims the benefit of U.S. Provisional Application 63/081,363 filed Sep. 22, 2020 which is hereby incorporated by reference in its entirety.

REFERENCE TO SEQUENCE LISTING SUBMITTED ELECTRONICALLY

This application contains a sequence listing, which is submitted electronically as an ASCII formatted sequence listing with a file name "689339_27_Sequence Listing", creation date of Sep. 20, 2023, and having a size of 30,410 bytes. The sequence listing electronically submitted is part of the specification and is herein incorporated by reference in its entirety.

BACKGROUND OF THE INVENTION

Obesity has become a major health issue in the United States. There's more than 40% Americans are considered to be overweight or obese by modern standards due to poor diet, lack of exercise or other unhealthy behavior. Obesity is an important underlying risk factor for developing other diseases such as heart disease, stroke, and diabetes. Typically, a modest decrease in excess body weight decreases the risk of developing certain obesity-associated diseases such as heart disease and diabetes.

Diabetes mellitus is a disorder in which the body does not produce enough or respond normally to insulin, causing blood sugar level to be abnormally high. Long term levels of high blood sugar often result in undesirable long-term health consequences including heart disease, stroke, poor overall circulation, and in severe cases, lower limb amputation. Treatment of diabetes usually involves controlling and/or reducing blood sugar levels through a combination of regular exercise and dietary control along with certain medications such as insulin and/or metformin.

One of the approaches used for treating diabetes and for glycemic control involves the use of glucagon-like peptide (GLP)-1 receptor agonists that target the incretin pathway. Glucagon-like peptide (GLP)-1 is a peptide hormone secreted by intestinal enteroendocrine cells. GLP1 exerts its main effect by stimulating glucose-dependent insulin release from the pancreatic islets. It has also been shown to slow gastric emptying, inhibit inappropriate post-meal glucagon release and reduce food intake.

However, GLP1 is quickly inactivated and/or degraded by the enzyme dipeptidyl peptidase 4 (DPP4) leading very short half-life of about 1.5 minutes. This is undesirable as it severely limits its effectiveness in regulating blood sugar levels. Longer-acting derivatives of GLP1 as well as GLP1 receptor agonists including fusion proteins comprising GLP1, provide an improved incretin effect and therefore, have been studied for diabetes control. Such GLP1 analogues, fusion proteins and GLP1 receptor agonists are well known in the art, with exemplary examples disclosed, for example, in U.S. Pat. No. 9,409,966, and published applications including US20160194371, US20170114115, US20170112904, US20160361390, US20150259416, WO2017074715, WO2016127887, EP3034514, EP2470198, and EP2373681.

GLP1 peptide variants and GLP1 receptor agonists that are resistant to degradation by DPP4 and other factors have also been explored. Previous work has shown that various amino acid substitutions at position 8 of GLP1 (7-37) make such peptides more resistant to DPP4, thus conferring a longer half-life. However, this approach still does come close to substantially fully protecting the GLP1 from DPP4 cleavage, and the middle part of the GLP1 molecule remains subject to other protease cleavage.

Certain such GLP1 variants and GLP1 receptor agonists are disclosed in US 2019/0091296 A1 to Wei et al. which is hereby incorporated by reference in its entirety. Although those variants provide the protection for the DPP4 cleavage, the middle part of GLP1 is still subject to be degraded by other proteases in the blood.

Accordingly, there is a need to develop GLP1 peptide variants and GLP1 receptor agonists that are further resistant to DPP4 and other protease degradation having improved pharmacokinetic properties and having increased potency and sustained invivo activity in glycemic control.

It therefore would be desirable to provide GLP1 peptide variants and GLP1 receptor agonists that are further resistant to degradation having improved pharmacokinetic properties and having increased potency and sustained in vivo activity in glycemic control.

It therefore would be desirable to provide GLP1 peptide variants with a protection sequence comprising the Extracellular domain (ECD) of the human GLP1 receptor to protect it from protease cleavage.

It therefore would be desirable to provide GLP1 peptide variants with a protection sequences that comprising an anti GLP1 antibody, preferably the Fab portions of the antibody, an nanobody or BiTE that can bind to GLP1 peptide variants and protect it from protease cleavage.

It therefore would be desirable to provide the protected GLP1 peptide variants with an anti-GLP1R targeting antibody having increased potency and sustained invivo activity in glycemic control.

SUMMARY OF THE INVENTION

One aspect of the present invention provides molecular technology for the protection of peptide-based drugs. The glucagon-like peptide-1 receptor (GLP1R) is a receptor protein typically found on beta cells of the pancreas and on neurons of the brain. It is involved in the control of blood sugar level by enhancing insulin secretion. In humans it is synthesized by the gene GLP1R, which is present on chromosome 6. It is a member of the glucagon receptor family of G protein-coupled receptors.

GLP1R includes two domains, one extracellular (ECD) that binds the C-terminal helix of GLP-1, and one transmembrane (TMD) domain that binds the N-terminal region of GLP-1. In the TMD domain, there is a fulcrum of polar residues that regulates the biased signaling of the receptor while the transmembrane helical boundaries and extracellular surface are a trigger for biased agonism.

According to one embodiment of the present invention, a fusion protein is provided wherein a receptor's extracellular domain (ECD) of the peptide, or a protection antibody (e.g., an antibody's Fab region, a nanobody or bispecific T-cell engager "BiTE" antibody in certain preferred embodiments) which binds to peptides, may be fused to the N-terminus of the peptide through a linker that contains a protease cleavage site (i.e., Factor Xa). With this approach, the fused receptor ECD or protection antibody may bind to the peptide and protect it from DPP4 and other protease degradation, thus conferring a longer half-life. In such embodiments, the fusion protein is, and remains inactive for the period before Factor Xa digestion removes the receptor ECD or protection antibody.

In one embodiment, an hGLP1R ECD structure consistent with the present invention was linked to the N-terminus of a GLP1 analogue (e.g., Eli Lily's TRULICITY™ drug although others may be used if desired) through a 3×G4S (SEQ ID NO: 14) linker followed by a protease cleavage site, for example Factor Xa. In such a fusion protein, the GLP1R ECD binds to GLP1, which confers two primary benefits: 1) substantially reduces or eliminates the DPP4 cleavage, and 2) protects the middle section of the GLP1 molecule from degradation due to other proteases in the blood.

Because the rate of release of the GLP-1 analogue by Factor Xa can be controlled by modifying the Factor Xa digestion sequence, a more constant GLP-1 analogue blood level may be achieved and thereby reduce undesirable side effects associated with varying blood sugar levels.

One particular way this may be accomplished includes certain modifications to portions of the Factor Xa digestion sequence (e.g., RKRR (SEQ ID NO: 15), RGER (SEQ ID NO: 16), RKR, RR etc.). Further, a point mutation (e.g., R108G) or deletion (position R108 to E116) may also be made in human GLP1R ECD in if desired to remove an internal Factor Xa cleavage site.

Before and after Factor Xa digestion, the fusion proteins of the present invention were tested for their ability to stimulate cAMP production in HEK cell line that stably expresses the human GLP1 receptor illustrating a significant improvement over previously known molecular structures and methods.

Other aspects of the invention are directed toward method of lowering blood sugar level by administering a pharmaceutical composition including one or more of the fusion proteins described herein in a therapeutically effective amount.

Such a method may be used to treat and/or prevent metabolic disorders including diabetes mellitus, obesity, insulin resistance, hypertension, dyslipidemia, Type 2 diabetes, Type 1 diabetes, prediabetes, cardiovascular disease, atherosclerosis, congestive heart failure, coronary heart disease, arteriosclerosis, peripheral artery disease, stroke, respiratory dysfunction, renal disease, fatty liver disease, non-alcoholic steatohepatitis (NASH), and metabolic syndrome.

The methods described above may also include administering the pharmaceutical composition in combination with a second therapeutic agent or therapy which may include insulin or insulin analogue, metformin, a thiazolidinedione, a sulfonylurea, a biguanide, chlorpropamide, a glinide, an alpha glucosidase inhibitor, nateglinide, a DPP4 inhibitor, pramlintide, sitagliptin, bromocriptine, a SGLT2 inhibitor, canagliflozin, an antihypertensive drug, a statin, aspirin, dietary modification, exercise, and a dietary supplement.

DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 3 is a general pictorial representation of the present invention showing Type 2 molecule as GLP1 analogue is released from the protection sequence in accordance with an aspect of the present invention.

FIG. 11A is graph illustrating IPGTT test results of diabetic test subjects in response to two molecular variants of molecules of the present invention on day 3.

FIG. 11B is graph illustrating IPGTT test results of diabetic test subjects in response to two molecular variants of molecules of the present invention on day 6.

FIG. 11C is graph illustrating IPGTT test results of diabetic test subjects in response to two molecular variants of molecules of the present invention on day 14.

DETAILED DESCRIPTION OF THE INVENTION

The following contains exemplary descriptions of methods and compounds in accordance with aspects of the present inventions. it will be to be understood, however, that the inventions herein are not limited to particular methods, and experimental conditions described, as such methods and conditions may vary. It is also will be understood that the terminology used herein is for the purpose of describing certain embodiments only, and is not intended to be limiting, but merely as a means for the expression of novel concepts of the invention and that the scope of the present invention will be limited only by the appended claims.

Unless defined otherwise, all technical and scientific terms used herein have the same meaning as commonly understood at the time of filing by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety including, but not limited to, U.S. Patent Publication 2019/0091296 A1 to Wei et al. which sets forth, among other things, commonly used definitions and sets forth commonly understood state of the art terminology and understanding which are used consistently herein including concepts of what is accepted understanding of bioequivalence.

Figure 2:
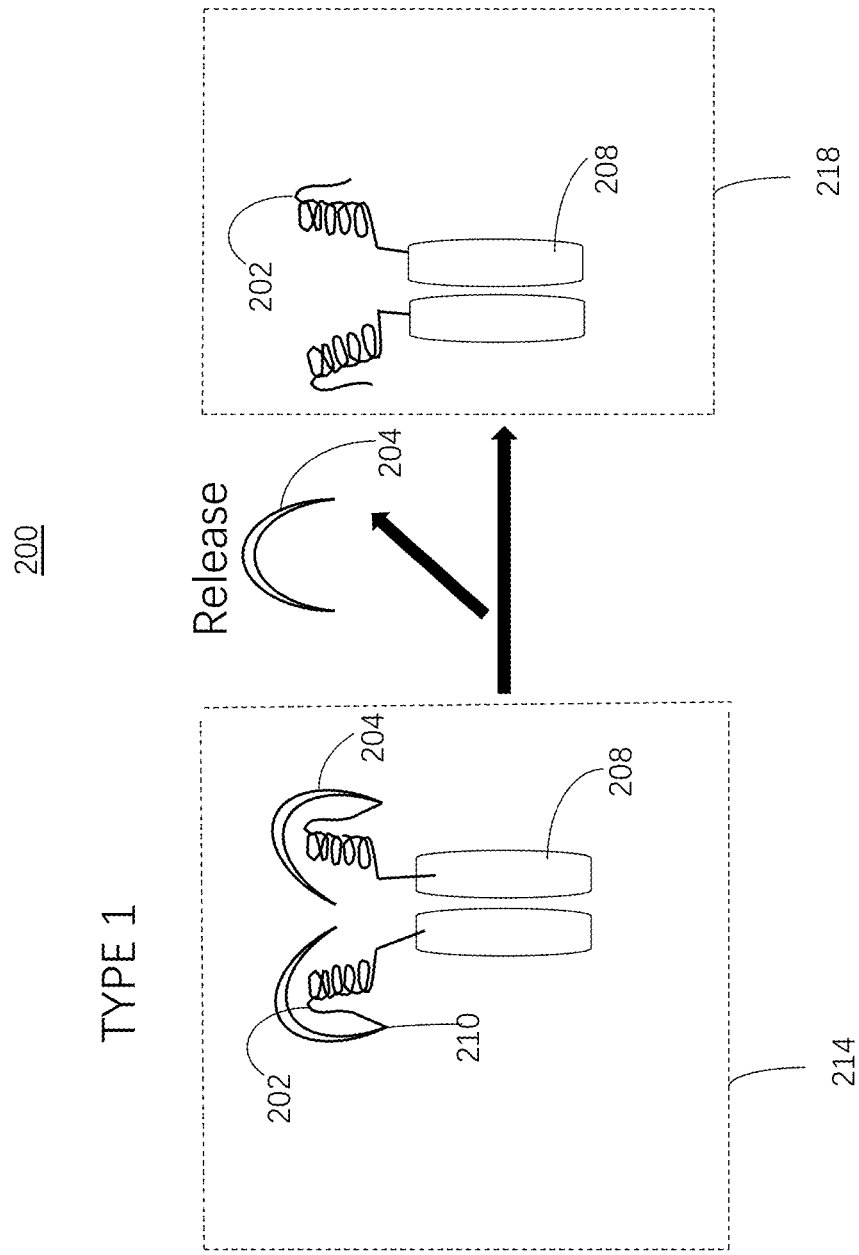
FIG. 2 is a general pictorial representation of the present invention showing Type 1 molecule as GLP1 analogue is released from the protection sequence in accordance with an aspect of the present invention.
Figures 4A, 4B, 4C, 4D:
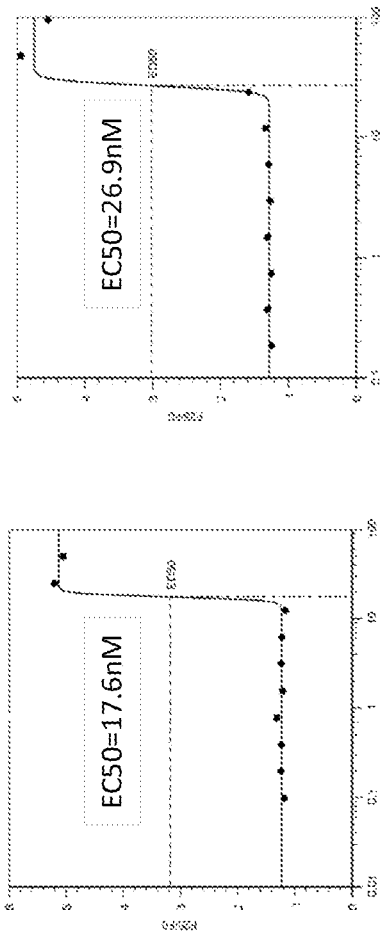
FIG. 4A-4D are graphs showing EC50 values of the GLP analog control molecules and molecules representing various embodiments of the of the present invention.

It is an object of the invention to improve the ability of a GLP-1 analogue type drugs to resist digestion-based degradation and thereby provide longer lasting effective glucose management in users. Certain known GLP-1 receptor agonists such as TRULICITY™ are fusion proteins that include two substantially identical, disulfide-linked chains, each containing an N-terminal GLP-1 analog sequence covalently linked to the Fc portion of a modified human immunoglobulin G4 (IgG4) heavy chain by a small peptide linker and is commonly produced using a mammalian cell (e.g., hamster ovary) culture.

The GLP-1 analog portion of such molecules is homologous to native human GLP-1 (7-37). Structural modifications are introduced in the GLP-1 part of the molecule responsible for interaction with DPP-4. Additional modifications were made in an area with a potential T-cell epitope and in the areas of the IgG4 Fc part of the molecule responsible for binding the high-affinity Fc receptors and half-antibody formation (generally referred to herein a the "Fc part"). This configuration activates the GLP-1 receptor, a membrane-bound cell-surface receptor coupled to adenylyl cyclase in pancreatic beta cells and increases intracellular cyclic AMP (cAMP) in beta cells leading to glucose-dependent insulin release with an extended half-life.

A general pictorial representation 100 illustrating aspects of the fusion protein concept in accordance with the present invention is shown in FIG. 1A-1C. As shown, molecule 102 is the base GLP-1 agonist molecule which may be fused to a protection sequence 104 (the ECD of GLP1R or an antibody's Fab region, a nanobody or bispecific T-cell engager "BiTE" antibody in certain preferred embodiments) through an amino acid linker region 110, which together may collectively form a protected GLP-1 molecule 106. In operation, protected molecule 106 may then be fused to the IgG4 Fc part 108 through an amino acid linker region (e.g., 3×G4S (SEQ ID NO: 14)) to create fusion protein 114 (Type 1), or to a suitable anti GLP1R antibody 112 to produce fusion protein 116 (Type 2).

It will be understood that any suitable GLP-1 agonist may be used for molecule 102 if desired, such as any Glucagon/secretin superfamily molecules which may include, but is not limited to, Glucagon, GLP-1, GLP-2, GIP, VIP, PACAP, Exendin-4, GLP1/GIP dual agonist and GLP1/GIP/Glucagon triple agonist, or other suitable peptide drugs, etc.

One of ordinary skill will readily understand and recognize that using the base construct and elements described above and illustrated in FIG. 1A-1C, at least dozens of variants of the fusion protein of the present invention may be produced if desired.

For example, in an Embodiment 1, the present invention may include a GLP1 variant comprising a GLP1R ECD fused to the N-terminal of TRULICITY™ though a 3×G4S (SEQ ID NO: 14) linker plus a Factor Xa protease digestion site.

In an Embodiment 2, the present invention may include the fusion protein of Embodiment 1, wherein the GLP1 ECD contains a mutation at the position of 108, from Arg to Gly, or to other amino acids to eliminate Factor Xa cleavage site.

In an Embodiment 3, the present invention may include the fusion protein of Embodiment 1, wherein the GLP1 ECD contains a 9 amino acids deletion at the C-terminus from position 108 to 116(RGERSSPEE) (SEQ ID NO: 3), in order to remove Factor Xa cleavage site.

In an Embodiment 4, the present invention may include a GLP1 variant comprising a Fab part of an anti GLP1R antibody, which is fused to the N-terminal of TRULICITY™ through a 3×G4S (SEQ ID NO: 14) linker plus a Factor Xa protease digestion site.

In an Embodiment 5, the present invention may include a GLP1 variant comprising a GLP1 protection nanobody fused to the N-terminal of TRULICITY™ through a 3×G4S (SEQ ID NO: 14) linker plus a Factor Xa protease digestion site.

In an Embodiment 6, the present invention may include a GLP1 variant comprising an anti GLP1 antibody in BiTE format fused to the N-terminal of TRULICITY™ through a 3×G4S (SEQ ID NO: 14) linker plus a Factor Xa protease digestion site.

In an Embodiment 7, the present invention may include the fusion proteins described in any of Embodiment 1 to 6, wherein the linker is 1×G4S (SEQ ID NO: 12), 2×G4S (SEQ ID NO: 13) or 3×G4S (SEQ ID NO: 14) plus the Factor Xa digestion site or its variant (i.e., RKRR (SEQ ID NO: 15), RGER (SEQ ID NO: 16), RKR, RR etc.), or other suitable protease digestion sites.

In an Embodiment 8, the present invention may include the fusion proteins of any Embodiment 1 to 7, wherein the GLP1 part of TRULICITY™ is select from one of the Glucagon/secretin superfamily includes, but not limited to: Glucagon, GLP-1, GLP-2, GIP, VIP, PACAP, Exendin-4, GLP1/GIP dual agonist and GLP1/GIP/Glucagon triple agonist.

In an Embodiment 9, the present invention may include the fusion proteins described in any of Embodiment 1 to 8, wherein the Fc part of TRULICITY™ is an anti GLP1R antibody, or an antibody against the receptor corresponding to the agonist has been used, or may be a bispecific antibody if a dual GLP1/GIP agonist is used.

As shown in FIG. 1A-1C, a protected fusion protein 106 is provided wherein a receptor's extracellular domain (ECD) of the peptide or a protection antibody 104 which binds to peptides 102 through linker 110 that contains a protease cleavage site (e.g., Factor Xa), may be fused to the N-terminus of the GLP1 variant fused to human Fc (e.g., TRULICITY™) to form Type 1 fusion protein 114, or a GLP1 variant fused to an antibody 112 to form Type 2 fusion protin 116. Accordingly, the receptor ECD or protection antibody 104 may bind to the peptide 102 and protect it from DPP4 and other protease degradation, thus conferring a longer half-life. In such embodiments, the fusion protein is, and remains inactive for the period before digestion removes receptor ECD or protection antibody 104.

As shown in FIG. 2, a more particularized version of the Type 1 molecule of FIG. 1B is depicted. As shown, a Type 1 molecule 214 constructed in accordance with the present invention, wherein the GLP1R ECD 204 was linked to the N-terminus of a GLP-1 analogue 208 (e.g., Eli Lily's TRULICITY™ drug although others such as Ozempic™ may be used if desired) through a linker 210 (3×G4S (SEQ ID NO: 14) followed by a protease cleavage site (e.g., Factor Xa)). These include SEQ IDs 6, 7, 8, 9, 10 and 11. In such a fusion protein, the GLP1R ECD binds to GLP1, which confers two primary benefits: 1) substantially reduces or eliminates the DPP4 cleavage, and 2) protects the middle section of the GLP1 molecule from degradation due to other proteases in the blood.

Because the rate of release of the GLP-1 analogue can be controlled by modifying the Factor Xa digestion through the modification of the Factor Xa sequence, a more constant GLP-1 analogue blood level may be achieved and thereby reduce undesirable side effects associated with varying blood sugar levels. This is generally depicted in FIG. 2 as which shows from left to right hGLP1R ECD protected Type 1 molecule 214 shedding protection sequence 204 in a controlled in predetermined manner as digestion progresses producing a released GLP1-hFc(TRULICITY™) molecule that provides users with substantially constant drug concentration as shown in FIGS. 4-11 discussed below.

One particular way was this may be accomplished includes certain modifications to portions of the Factor Xa digestion sequence (e.g., RKRR (SEQ ID NO: 15), RGER (SEQ ID NO: 16), RKR, RR etc.). Further, a point mutation (R108G) or deletion (position R108 to E116) may also be made in human GLP1R ECD in if desired to remove an internal Factor Xa cleavage site.

Figure 1:
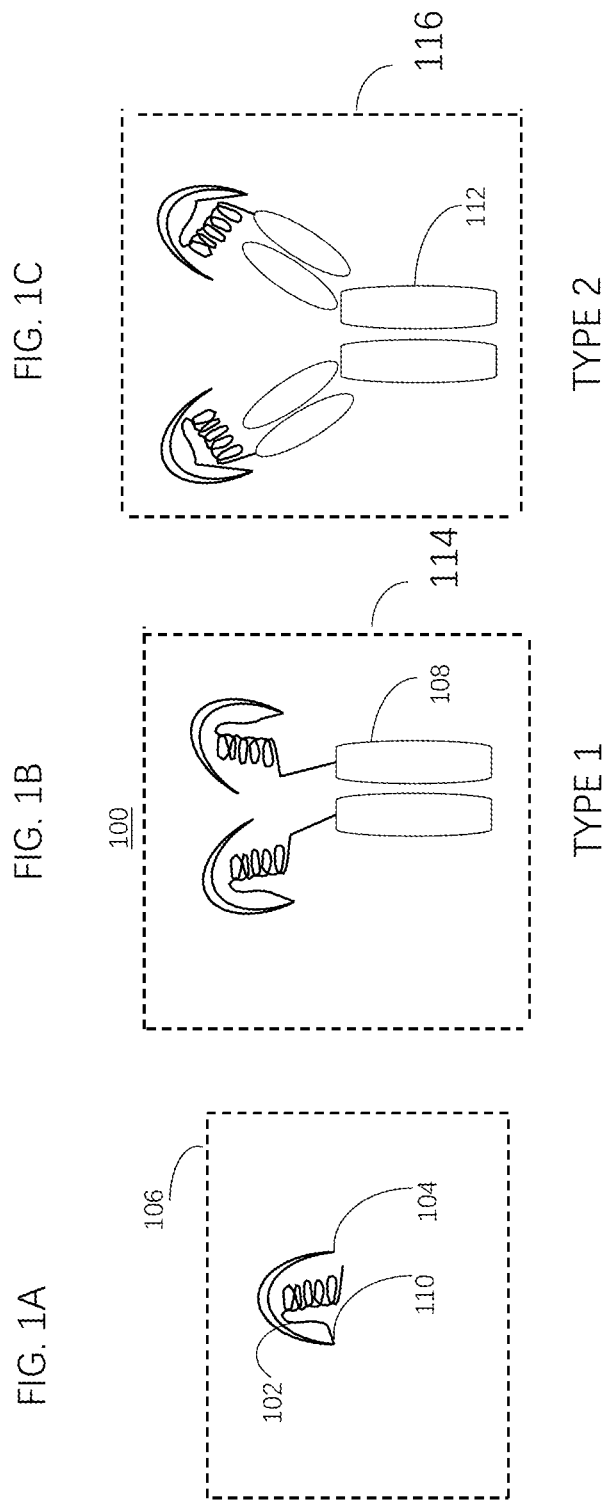
FIG. 1A-1C is a general pictorial representation of the present invention showing the general construction of embodiments of the fusion protein of the present invention.

Similarly, as shown in FIG. 3, a more particularized version of the Type 2 molecule of FIG. 1C is depicted. As shown, an hGLP1 antibody protected Type 2 molecule 314 constructed in accordance with the present invention. A protection sequence 304 (e.g., hGLP1R ECD or an anti GLP1 antibody) was linked to the N-terminus of a GLP-1 agonist 302 through 3×G4S (SEQ ID NO: 14) linker 310 contains a protease cleavage site (e.g., Factor Xa) to form molecule 306, then molecule 306 was linked to the N-terminus of the light chain of an anti-GLP1R targeting antibody to form fusion protein 314. In such a fusion protein, the GLP1R ECD binds to GLP1, which, as above in FIG. 3 confers two primary benefits: 1) substantially reduces or eliminates the DPP4 cleavage, and 2) protects the middle section of the GLP1 molecule from degradation due to other proteases in the blood.

Because the rate of release of the GLP-1 analogue can be controlled by modifying the Factor Xa digestion through the modification of Factor Xa sequence, a more constant GLP-1 analogue blood level may be achieved and thereby reduce undesirable side effects associated with varying blood drug concentration levels. This is generally depicted in FIG. 3 which shows from left to right the Type 2 molecule 314 shedding protection sequence 304 in a controlled in predetermined manner as digestion progresses producing a released GLP1-antibody molecule 318 that provides users with substantially constant blood drug concentration as shown in the charts below.

Example 1

The following examples reflects experiments conducted on Aug. 1, 2019 through Dec. 31, 2019 which was performed by outsourced CRO companies.

Reagents Used and Lot Numbers:
  Eli Lilly TRULICITY™ (Lot #02448599)
  pTG1: hFc (lot #U6443DH140S05/P90011809)
  pTG3: hGLP1R ECD-3×G4S-RKRR-TRULICITY™ (lot #U5585DH140S05/P90011809)
  p7: hGLP1R ECD(R108G)-3×G4S-RGER-TRULICITY™ (lot #U2243DL140-4/P9EA001)
  p8: hGLP1R ECD(R108G)-3×G4S-TRULICITY™ (lot #U2243DL140-9/P9EA001)
  p9: hGLP1R ECD (1-116)-3×G4S-RGER-TRULICITY™ (lot U2243DL140-14/P9EA001)
  p10: hGLP1R ECD(R108G)-3×G4S-RR-TRULICITY™ (lot #U2243DL140-19/P9EA001)
  p11: hGLP1R ECD(R108G)-3×G4S-RKR-TRULICITY™ (lot #U2243DL14024/P9EA001)
Experimental Procedure (Include Description of Relevant Cell Lines, Proteins, Reagents, and Instrument Type and Model):

A hGLP1R ECD molecule (SEQ ID NO 3) was linked to the N-terminus of TRULICITY™ through a linker contains a 3×G4S (SEQ ID NO: 14) and a protease cleavage site (Factor Xa, NEB lot #P8010S).

To better control releasing time of active TRULICITY™, several modifications were made for the Factor Xa cleavage sequence (e.g., RGER (SEQ ID NO: 16), RKR, RR etc.). A point mutation(R108G) (SEQ ID NO 4) or deletion (position R108 to E116) (SEQ ID NO 5) were made in human GLP1R ECD in order to remove a Factor Xa cleavage site.

For cAMP bioassay, the HEK293-CNG-HuGLP1R stable cells were seeded into 96-well assay plates at 70,000 cells/well in OPTIMEM supplemented with 10% FBS and then incubated at 37° C. in 5% CO2 overnight. The following day, 50 uM phosphodiesterase inhibitor R020-1724 in 1×Membrane Potential Dye (Creative Biogene, lot #FMD10) was added and incubated at 37° C. for 2 hours, and then read with fluorescence microplate reader (F0, Excitation/Emission=530 nm/570 nm) (MD Paradigm).

To determine the dose response of the test proteins, substantially all proteins were predigested with Factor Xa to release active TRULICITY™. Next, TRULICITY™, and released pTG3, p7, p8, p9, p10 and p11 (SEQ IDs 6-11 respectively) were added to cells at concentrations ranging from 0.001 nM to 100 nM, incubate at 37° C. for 25 minutes before read with fluorescence microplate reader (F25). The results were analyzed using nonlinear regression (three parameter) with Prism 6 software (GraphPad) to obtain EC50 values.

For ELISA, the plate was coated with Mouse anti-human IgG (Fc) (CELLWAYLAB lot #C010202) at 4ug/ml, 4° C. overnight, block with 0.2% BSA/0.1% PC/0.1% at room temperate for one hour, then samples prepared from mouse serum were added and incubated at room temperate for an hour. The TRULICITY™ is used as the standard curve. Anti GLP-1 antibody (ThermoFisher, Catalog #: ABS03310B005) is used for detecting active TRULICITY™. Next, after adding TMB for 10 minutes, the reaction was stopped by 2M H2SO4, and read at 450 nm with plate reader (CMax Plus, Molecular Devices).

Figure 6:
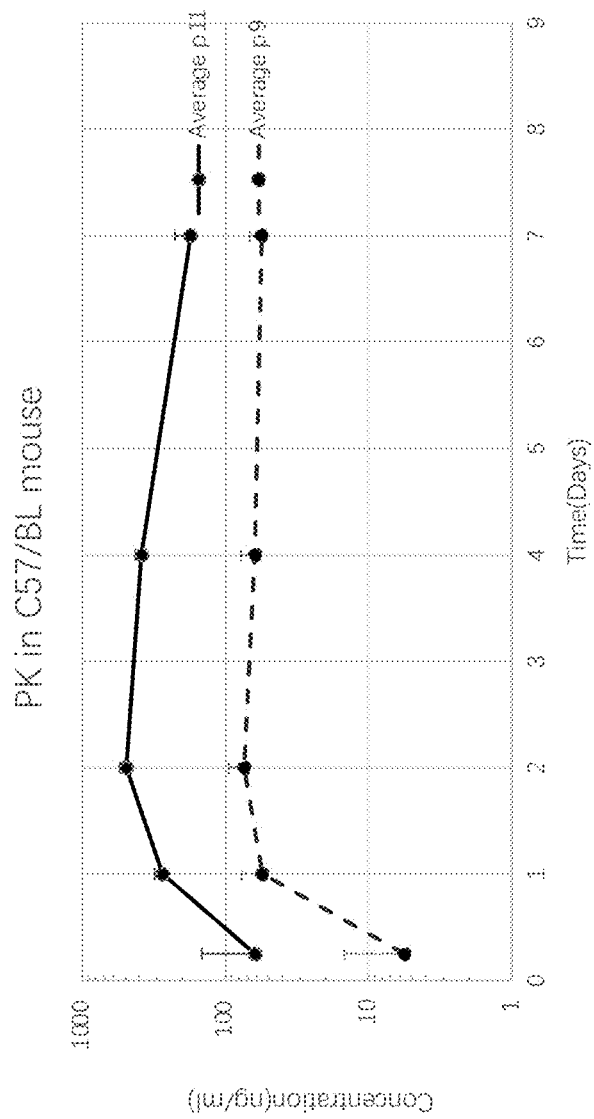
FIG. 6 is graph showing the pharmacokinetic profiles of two molecules constructed in accordance with embodiments of the present invention over 7 days.
Figure 7:
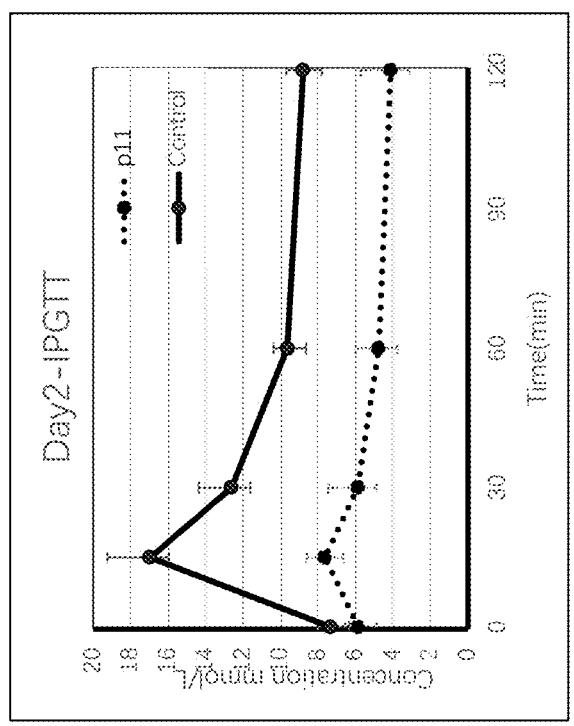
FIG. 7 is graph showing glucose levels of test subject in response to a molecule of one embodiment of the present invention on day 2.
Figure 8:
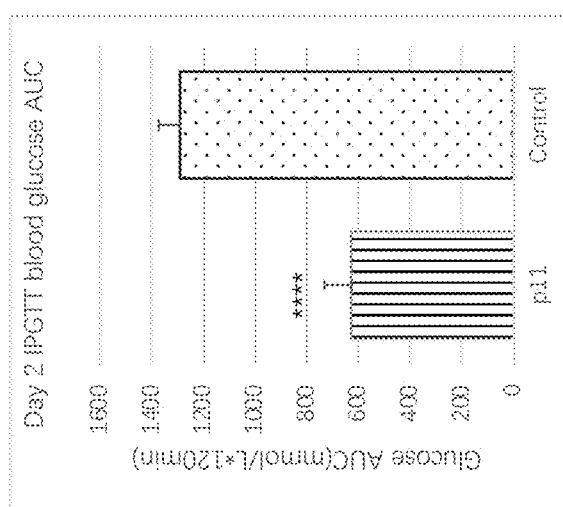
FIG. 8 is graph showing glucose AUC of test subject in response to a molecule of one embodiment of the present invention on day 2 compared to a control.
Figure 9:
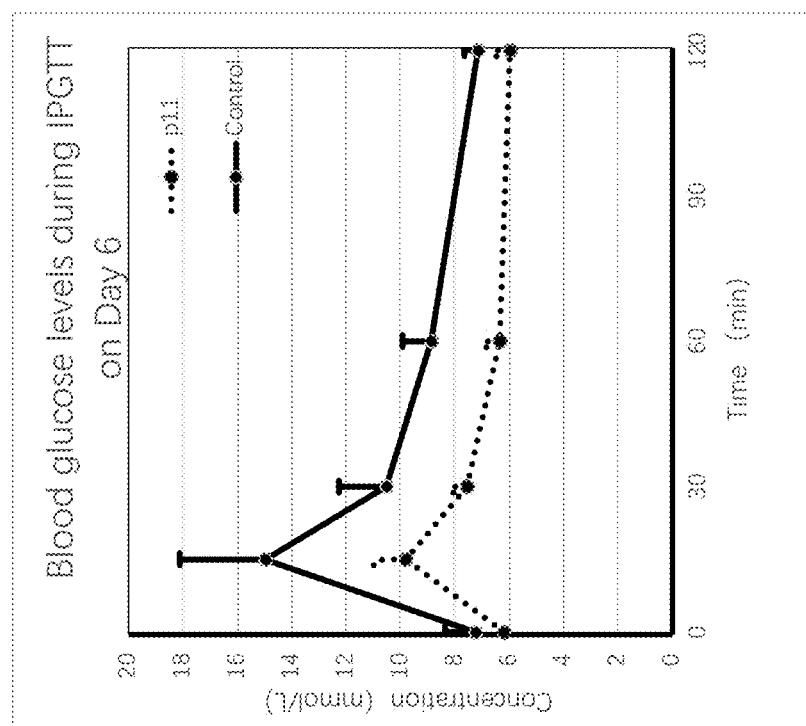
FIG. 9 is graph showing glucose levels of test subject in response to a molecule of one embodiment of the present invention on day 6.
Figure 10:
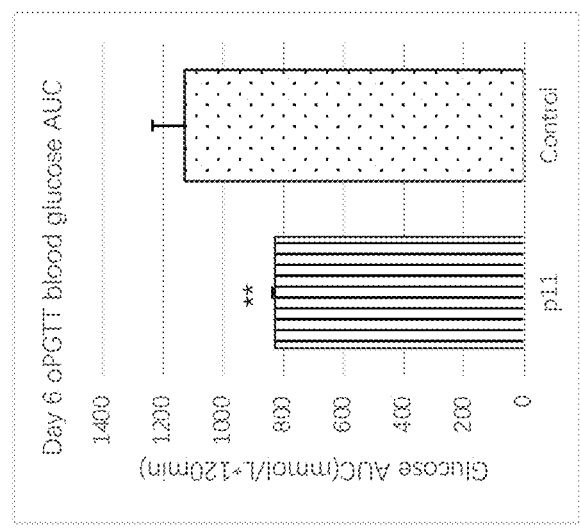
FIG. 10 is graph showing glucose AUC of test subject in response to a molecule of one embodiment of the present invention on day 6 compared to a control.

Pharmacokinetic profiles of p9 and p11 (SEQ IDs 9 and 11 respectively) in C57/BL Mice (Beijing Vital River Laboratory Animal Technology Company) were studied after subcutaneous (SC) administration of 200 nmol/kg drugs. Blood is drawn from the test subjects (4 mice per group) at various time at 6 h, day 1, 2, 4 and 7 after dosing. Serum is collected from each sample and analyzed by N-terminal specific ELISA which only detect active TRULICITY™. The blood drug concentration at each time point are shown in FIG. 6.

The effect of p9 and p11 on glucose tolerance was determined in both C57/BL and BKS/DB mouse (JiangSu GemPharmatech Company). Each group (4 mice per group) received a single subcutaneous injection of hFc control pTG1, p9, p11, and TRULICITY™ at 200 nmol/kg. Intraperitoneal glucose tolerance tests (IPGTT) were performed on Day 3, Day 6 and 14 after overnight fasting with blood glucose measurements at 0, 15, 30, 60, and 120 minutes. Mean SEM of blood glucose levels at each time point and glucose area under curve (AUC) were calculated for each group and shown in FIGS. 7-11. Excel t-test was used to assess the significance to the control group, *: $p<0.05$, : $p<0.01$, *: $p<0.001$, **: $p<0.0001$ Invitro Results Summary and Conclusions As shown in the Table 1 and FIG. 4A-4D**, TRULICITY™, and the released p7, p9 and p11 show EC50 values of 22 nM, 25 nM, 17.6 nM and 26.9 nM, respectively, for GLP1R activation. The EC50 for released pTG3 and p10 is only 617 nM and 120 nM, indicating the Factor Xa digestion were not at predicted sites. This was confirmed by N-terminal amino acids sequence analysis. The EC50 for p8 is undetectable because there is no Factor Xa digestion site, therefore the active TRULICITY™ cannot be released.

Figure 5:
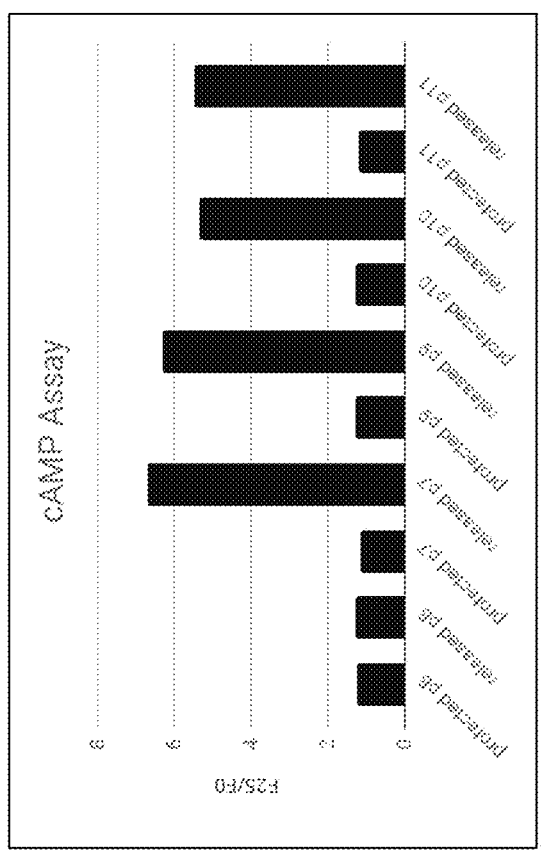
FIG. 5 is bar chart showing of the cAMP Assay showing activity of embodiments of the present after the GLP1 analogue is released during digestion.

As show in FIG. 5, the p7, p9, p10 and p11 only show activities after Factor Xa digestion (released). The p8 (SEQ ID8) negative control shows no cAMP activity because it contains no Factor Xa digestion site and the active TRULICITY™ couldn't be released.

TABLE 1

EC50 for released GLP1 Fusion Proteins

| GLP1 fusion proteins | EC50 |
| --- | --- |
| hGLP1R ECD-3xG4S-RKRR-TRULICITY ™ (pTG3, lot# U5585DH140S05/P90011809) | 617 nM |
| hGLP1R ECD(R108G)-3xG4S-RGER-TRULICITY ™ (p7, lot# U2243DL140-4/P9EA001) | 25 nM |
| hGLP1R ECD(R108G)-3xG4S TRULICITY ™ (p8, lot# U2243DL140-9/P9EA001) | undetectable |
| hGLP1R ECD(1-116)-3xG4S-RGER-TRULICITY ™ (p9, lot U2243DL140-14/P9EA001) | 17.6 nM |
| hGLP1R ECD(R108G)-3xG4S-RR-TRULICITY ™ (p10, lot# U2243DL140-19/P9EA001) | 120 nM |
| hGLP1R ECD(R108G)-3xG4S-RKR-TRULICITY ™ (p11, lot# U2243DL140-24/P9EA001) | 26.9 nM |
| Eli Lilly's TRULICITY ™ (Lot#) | 22 nM |

Invivo Results Summary and Conclusions

FIG. 6 shows Pharmacokinetic profiles of released p9 and p11 in C57/BL Mice after subcutaneous (SC) administration of 200 nmol/kg. The half-life for released p11 is 6 days, the half-life for p9 is longer than 7 days because 75% of released p9 is still detected at day 7. Both proteins show relative constant blood drug concentration from day 1 to day 7.

FIGS. 7-10 show favorable IPGTT results in C57/BL mice, that is, a single administration of p11 variant of the present invention provided significant glucose reductions at day 2 and 6.

Similarly, FIGS. 11A, 11B, and 11C show the IPGTT results in diabetic BKS/DB mice, that is, a single administration of p9 and p11 variants of the invention provided significant glucose reductions at day 3, day 6 and day 14.

Bioequivalents

The GLP1 receptor agonists of the present invention may include proteins having amino acid sequences that may vary from those of the described GLP1 receptor agonists, but that retain the ability to bind GLP1 receptor. Such variant GLP1 receptor agonists may comprise one or more additions, deletions, or substitutions of amino acids when compared to parent sequence but exhibit biological activity that is essentially equivalent to that of the described GLP1 receptor agonists. Similarly, the GLP1 receptor agonist-encoding DNA sequences of the present invention may encompass sequences that comprise one or more additions, deletions, or substitutions of nucleotides when compared to the disclosed sequence, but that encode a GLP1 receptor agonist that is essentially bioequivalent to a GLP1 receptor agonist of the invention.

Two proteins may be considered bioequivalent if, for example, they are pharmaceutical equivalents or pharmaceutical alternatives whose rate and extent of absorption are substantially the same do not exhibit a significant difference when administered at the same molar dose under similar experimental conditions, which may include either single dose or multiple doses. Some proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two GLP1 receptor agonist proteins are bioequivalent if there are no clinically meaningful differences in their safety, purity, potency or efficacy.

In one embodiment, two GLP1 receptor agonist proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two GLP1 receptor agonist proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the protein (or its target) is measured as a function of time; and (d) in a well-controlled clinical trial that establishes safety, efficacy, or bioavailability or bioequivalence of an antigen-binding protein.

Bioequivalent variants of the GLP1 receptor agonist proteins of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent proteins may include variants comprising amino acid changes, which modify the glycosylation characteristics of the proteins, e.g., mutations that eliminate or remove glycosylation.

Therapeutic Administration and Formulations

The invention provides therapeutic compositions comprising the GLP1 receptor agonists. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of GLP1 receptor agonist may vary depending upon the age and the size of a subject to be administered, target disease, conditions, route of administration, and the like. When an antigen-binding protein of the present invention is used for treating a disease or disorder in an adult patient, or for preventing such a disease, it is advantageous to administer the antigen-binding protein of the present invention normally at a single dose of about 0.001 to about 100 mg/kg body weight, more preferably about 0.001 to about 60, about 0.01 to about 10, or about 0.01 to about 1 mg/kg body weight. Depending on the severity of the condition, the frequency and the duration of the treatment can be adjusted. In certain embodiments, the antigen-binding protein or antigen-binding fragment thereof of the invention can be administered as an initial dose of at least about 0.001 mg to about 100 mg, about 0.001 to about 50 mg, about 0.005 to about 50 mg, about 0.01 to about 40 mg, to about 30 mg, or to about 10 mg. In certain embodiments, the initial dose may be followed by administration of a second or a plurality of subsequent doses of the GLP1 receptor agonist in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the GLP1 receptor agonists of the present invention is also contemplated herein. Protein-conjugated nanoparticles may be used both for therapeutic and diagnostic applications. Nanoparticles may be developed and conjugated to antigen-binding proteins contained in pharmaceutical compositions to target cells. Nanoparticles for drug delivery have also been described in, for example, U.S. Pat. No. 8,257,740, or U.S. Pat. No. 8,246,995, each incorporated herein in its entirety.

If desired, the pharmaceutical compositions or treatments of the present invention may be delivered in a controlled release system. In one embodiment, a pump may be used. In other embodiments, polymeric materials can be used. In yet other embodiments, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen or wand type delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the GLP1 receptor agonist contained is generally about 0.001 to about 100 mg per dosage form in a unit dose; especially in the form of injection, it is preferred that the GLP1 receptor agonist is contained in about 0.001 to about 100 mg and in about 0.01 to about 100 mg for the other dosage forms.

Therapeutic Uses of the GLP1 Receptor Agonists

The GLP1 receptor agonists of the present invention are useful for the treatment, and/or prevention of certain adverse medical conditions associated with hyperglycemia including diabetes. It also may be useful for lessening the severity of at least one symptom associated with such conditions. This may include, for example administering it at a therapeutic dose to a patient with diabetes (e.g., type 2 diabetes).

Furthermore, in some embodiments, the GLP1 receptor agonists of the invention are useful to treat subjects suffering from health problems form the group comprising diabetes mellitus, obesity, insulin resistance, hypertension, dyslipidemia, Type 2 diabetes, Type 1 diabetes, pre-diabetes, cardiovascular disease, atherosclerosis, congestive heart failure, coronary heart disease, arteriosclerosis, peripheral artery disease, stroke, respiratory dysfunction, renal disease, fatty liver disease, metabolic syndrome and similar or associated conditions.

In some embodiments, the GLP1 receptor agonists of the invention are useful to treat subjects that are overweight, obese and/or prevent or treat one or more obesity-associated disorders such as heart disease, stroke, and diabetes.

In some embodiments, the GLP1 receptor agonists of the invention are useful to treat subjects suffering from diabetes and/or prevent one or more complications of associated with diabetes such as heart disease, stroke, kidney disease, retinopathy, blindness and peripheral nerve damage.

It will be understood that one or more GLP1 receptor agonist fusion proteins of the present invention may be used as a preventive measure for patients in danger of developing diabetes (e.g., from type 2 diabetes). Such risks include, but are not limited to, patients of advanced age, pregnant women, and/or other risk factors including family history of obesity, high blood cholesterol, smoking, excessive alcohol consumption, and/or lack of exercise.

In a further embodiment, the proteins of the invention may be used for the preparation of a pharmaceutical composition or medicament for treating patients suffering from a disease or disorder such as diabetes and obesity. In other embodiments of the invention, the GLP1 receptor agonists may be used as complimentary or supplemental therapy with any other suitable therapy known to those skilled in the art useful for treating or ameliorating a disease or disorder associated with hyperglycemia such as diabetes (e.g., type 2 diabetes).

Combination Therapies

Combination therapies contemplated by the present invention may include a GLP1 receptor agonist of the invention and any suitable additional therapeutic agent that may be advantageously combined therewith, such as GLP1 receptor agonist of the invention, or a biologically active fragment of the invention as would be appreciated by one of ordinary skill in the art. Further combination may include the GLP1 receptor agonists of the present inventio combined synergistically with one or more drugs or therapy used to treat any disease or disorder associated with hyperglycemia (e.g., diabetes). In some embodiments, the GLP1 receptor agonists of the invention may be combined with one or more other therapeutic agent(s) to reduce blood sugar levels in a subject, or to ameliorate one or more symptoms of diabetes.

The GLP1 receptor agonists of the present invention may be used in combination with an insulin (insulin or an insulin analog), insulin sensitizers such as biguanides (e.g., metformin), and thiazolidinediones (e.g., rosiglitazone), insulin secretagogues such as sulphonylureas (e.g., chlorpropamide), and glinides (e.g., nateglinide), alpha-glucosidase inhibitors (e.g., acarbose), dipeptidyl peptidase 4 (DPP4) inhibitors (e.g., sitagliptin), pramlinitide, bromocriptine, sodium glucose cotransporter 2 (SGLT-2) inhibitors (e.g., canagliflozin), an anti-hypertensive drug (e.g., an angiotensin-converting enzyme inhibitor, an angiotensin receptor blocker, a diuretic, a calcium channel blocker, an alpha-adrenoceptor blocker, an endothelin-1 receptor blocker, an organic nitrate, and a protein kinase C inhibitor), a statin, aspirin, a different GLP1 receptor agonist, a dietary supplement or any other therapy (e.g., exercise) to treat or manage diabetes.

In yet other embodiments, the GLP1 receptor agonists may be administered in combination with a one or more therapeutic agent(s) including: insulin, an insulin analog, metformin, rosiglitazone, pioglitazone, chlorpropamide, glibenclamide, glimepiride, glipizide, tolazamide, tolbutamide, nateglinide, repaglinide, acarbose, miglitol, exenatide, liraglutide, albiglutide, dulaglutide, sitagliptin, saxagliptin, linagliptin, alogliptin, pramlinitide, bromocriptine quick-release, canagliflozin, dapagliflozin, empagliflozin, diet modifications and exercise.

As used herein, the term "in combination with" means that additional therapeutically active component(s) may be administered prior to, concurrent with, or after the administration of the GLP1 receptor agonist of the present invention. The term "in combination with" also includes sequential or concomitant administration of a GLP1 receptor agonist and a second therapeutic agent.

The additional therapeutically active component(s) may be administered to a subject prior to administration of a GLP1 receptor agonist of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of a GLP1 receptor agonist of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of a GLP1 receptor agonist of the present invention. "Concurrent" administration, for purposes of the present invention, includes, e.g., administration of a GLP1 receptor agonist and an additional therapeutically active component to a subject in a single dosage form, or in separate dosage forms administered to the subject within about 30 minutes or less of each other. If administered in separate dosage forms, each dosage form may be administered via the same route (e.g., both the GLP1 receptor agonist and the additional therapeutically active component may be administered intravenously, etc.); alternatively, each dosage form may be administered via a different route (e.g., the GLP1 receptor agonist may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of a GLP1 receptor agonist "prior to", "concurrent with," or "after" (as those terms are defined herein above) administration of an additional therapeutically active component is considered administration of a GLP1 receptor agonist "in combination with" an additional therapeutically active component.

The present invention includes pharmaceutical compositions in which a GLP1 receptor agonist of the present invention is co-formulated with one or more of the additional therapeutically active component(s) as described elsewhere herein.

All publications and patent documents disclosed or referred to herein are incorporated by reference in their entirety. The foregoing description has been presented only for purposes of illustration and description. This description is not intended to limit the invention to the precise form disclosed. Indeed, various modifications of the invention in addition to those described herein will become apparent to those skilled in the art from the foregoing description and the accompanying figures. Such modifications are intended to fall within the scope of the appended claims.

It will be understood that the molecular structures and methods disclosed herein are merely illustrative and are not meant to be comprehensive or necessarily performed in the order or exact fashion shown. Persons skilled in the art will appreciate that the present invention can be practiced by other than the described embodiments, which are presented for purposes of illustration rather than of limitation, and the present invention is limited only by the claims which follow.

The below Sequence ID is also submitted in an ASCII text file named "YW-001_SEQ" and is specifically incorporated herein by reference.

What is claimed is:

1. A fusion protein comprising:
    a protection sequence for a Glucagon-like peptide-1 (GLP-1) analogue to impede in vivo cleavage, inactivation or degradation;
    a first amino acid linker containing a protease cleavage site configured for coupling the protection sequence to the GLP-1 analogue, wherein the first linker comprises an amino acid sequence GGGGS (SEQ ID NO: 12), GGGGSGGGGS (SEQ ID NO: 13) or GGGGSGGGGSGGGGS (SEQ ID NO: 14);
    the GLP-1 analogue,
    a second linker, wherein the second linker comprises an amino acid sequence GGGGS (SEQ ID NO: 12), GGGGSGGGGS (SEQ ID NO: 13) or GGGGSGGGGSGGGGS (SEQ ID NO: 14); and
    a Fc part or a GLP-1 Receptor targeting antibody,
    wherein the protection sequence comprises:
        (a) a GLP-1 Receptor extracellular domain (ECD), wherein the GLP-1 Receptor ECD includes a point mutation or a deletion to eliminate Factor Xa cleavage site;
        (b) an anti GLP-1 nanobody;
        (c) a Fab region of an anti GLP-1 antibody; or
        (d) an anti GLP-1 bispecific T-cell engager (BiTE) antibody,
    wherein the protection sequence binds to the GLP-1 analogue and protects the GLP-1 analogue from protease cleavage, and
    wherein the protection sequence is fused to the N-terminus of the GLP-1 analogue through the first linker,
    wherein the Fc part or the GLP-1 Receptor targeting antibody is fused to the C-terminus of the GLP-1 analogue through the second linker.

2. The fusion protein of claim 1, wherein the protease cleavage sequence is for Factor Xa or the protease cleavage sequence is a variant of Factor Xa digestion site, wherein the variant of Factor Xa digestion site comprises RKRR (SEQ ID NO: 15), RGER (SEQ ID NO: 16), RKR, or RR.

3. A pharmaceutical comprising a fusion protein of claim 1 and a pharmaceutically acceptable carrier or diluent.

4. A method of lowering blood sugar level comprising administering a pharmaceutical composition comprising a therapeutically effective amount of the protein of claim 1 to a subject in need thereof.

5. The method of claim 4, wherein the subject has a disease or disorder selected from the group consisting of diabetes mellitus, obesity, insulin resistance, hypertension, dyslipidemia, Type 2 diabetes, Type 1 diabetes, prediabetes, cardiovascular disease, atherosclerosis, congestive heart failure, coronary heart disease, arteriosclerosis, peripheral artery disease, stroke, respiratory dysfunction, renal disease, fatty liver disease, non-alcoholic steatohepatitis (NASH), and metabolic syndrome.

6. The method of claim 4, wherein the pharmaceutical composition is administered in combination with a second therapeutic agent or therapy.

7. The method of claim 4, wherein the second therapeutic agent or therapy is selected from the group consisting of an insulin or insulin analogue, metformin, a thiazolidinedione, a sulfonylurea, a biguanide, chlorpropamide, a glinide, an alpha glucosidase inhibitor, nateglinide, a DPP4 inhibitor, pramlintide, sitagliptin, bromocriptine, a SGLT2 inhibitor, canagliflozin, an antihypertensive drug, a statin, aspirin, dietary modification, exercise, and a dietary supplement.

8. The method of claim 4, wherein the pharmaceutical composition is administered subcutaneously, intravenously, intradermally, intraperitoneally, orally, or intramuscularly.

9. A method of treating or ameliorating at least one symptom, indication or complication of Type 2 diabetes, the method comprising administering a pharmaceutical composition comprising a therapeutically effective amount of the protein of claim 1 to a subject in need thereof.

10. The method of claim 9, wherein the at least one symptom, indication or complication is selected from the group consisting of high blood sugar level, excessive thirst, increased urination, presence of ketones in urine, fatigue, weight fluctuations, blurred vision, slow healing sores, frequent infections, swollen or tender gums, obesity, heart disease, stroke, kidney disease, eye disease, nerve damage and high blood pressure.

11. A fusion protein comprising:
a protection sequence for a peptide to impede in vivo cleavage, inactivation or degradation;
a first amino acid linker containing a protease cleavage site configured for coupling the protection sequence to the peptide, wherein the first linker comprises an amino acid sequence GGGGS (SEQ ID NO: 12), GGGGSGGGGS (SEQ ID NO: 13) or GGGGSGGGGSGGGGS (SEQ ID NO: 14);
the peptide,
a second linker, wherein the second linker comprises an amino acid sequence GGGGS (SEQ ID NO: 12), GGGGSGGGGS (SEQ ID NO: 13) or GGGGSGGGGSGGGGS (SEQ ID NO: 14); and
a Fc part or an antibody against a receptor corresponding to the peptide,
wherein the peptide is selected from the group consisting of Glucagon, GLP-1, GLP-2, GIP, VIP, PACAP, and Exendin-4,
wherein the protection sequence comprises a nanobody, a Fab region of an antibody, or a bispecific T-cell engager (BiTE) antibody,
wherein the protection sequence binds to the peptide and protects the peptide from protease cleavage, and
wherein the protection sequence is fused to the N-terminus of the peptide through the first linker,
wherein the Fc part or the antibody against a receptor corresponding to the peptide is fused to the C-terminus of the peptide through the second linker.

12. A fusion protein comprising:
a protection sequence for a GLP-1/GIP dual agonist to impede in vivo cleavage, inactivation or degradation;
a first amino acid linker containing a protease cleavage site configured for coupling the protection sequence to the GLP-1/GIP dual agonist;
the GLP-1/GIP dual agonist,
a second linker, wherein the second linker comprises an amino acid sequence GGGGS (SEQ ID NO: 12), GGGGSGGGGS (SEQ ID NO: 13) or GGGGSGGGGSGGGGS (SEQ ID NO: 14); and
an anti GLP-1 Receptor targeting antibody, an anti GIP Receptor targeting antibody, or a bispecific antibody targeting GLP-1 Receptor and GIP Receptor
wherein the protection sequence comprises a nanobody, a Fab region of an antibody, or a bispecific T-cell engager (BiTE) antibody,
wherein the protection sequence binds to the GLP-1/GIP dual agonist and protects the GLP-1/GIP dual agonist from protease cleavage,
wherein the protection sequence is fused to the N-terminus of the GLP-1/GIP dual agonist through the first linker,
wherein the anti GLP-1 Receptor targeting antibody, the anti GIP Receptor targeting antibody, or the bispecific antibody targeting GLP-1 Receptor and GIP Receptor is fused to the C-terminus of the GLP-1/GIP dual agonist through the second linker.

\* \* \* \* \*